United States Patent
Meng et al.

(10) Patent No.: US 8,021,578 B2
(45) Date of Patent: Sep. 20, 2011

(54) FUSED THIOPHENE ACENES AND ORGANIC SEMICONDUCTORS MADE THEREFROM

(75) Inventors: Hong Meng, Wilmington, DE (US); Fangping Sun, Boothwyn, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 442 days.

(21) Appl. No.: 12/342,306

(22) Filed: Dec. 23, 2008

(65) Prior Publication Data
US 2009/0166590 A1    Jul. 2, 2009

Related U.S. Application Data

(60) Provisional application No. 61/009,401, filed on Dec. 28, 2007.

(51) Int. Cl.
*H01L 35/24* (2006.01)
(52) U.S. Cl. .......................... 252/500; 549/41
(58) Field of Classification Search ................. 252/500; 549/41, 456; 556/406; 568/3, 12
See application file for complete search history.

(56) References Cited

U.S. PATENT DOCUMENTS
6,621,098 B1    9/2003    Jackson et al.

OTHER PUBLICATIONS

S. Darses et al., Potassium Trifluoro(Organo)Borates: New Perspectives in Organic Chemistry, Eur. J. of Org. Chem., 2003, vol. 22:4313-4327.
W. A. Herrmann et al., C-C Coupling Reactions (Heck, Stille, Suzuki, Etc.) Aqueous-Phase Organometallic Catalysis, 2nd Edition, 2004, pp. 511-523.
A. N. Cammidge et al., Octaalkyl- and Octaalkoxy-2,3-Naphthalocyanines, Journal of Porphyrins and Phthalocyanines, 1997, vol. 1:77-86.
Sze, Physics of Semiconductor Devices, 2nd Edition, 1981, John Wiley & Sons (Book Not Included).
Peter Van Zant, Microchip Fabrication, 4th Edition, 2000, McGraw-Hill, New York (Book Not Included).
P. Hodge et al., Synthesis of Poly(Anthracene-2,6-Diyl) and a Copolymer Containing Alternately Anthracene-2,6-Diyl and P-Phenylene Units, Chem. Commun., 1997, pp. 73-74.

*Primary Examiner* — Harold Y Pyon
*Assistant Examiner* — Timothy Chiang

(57) ABSTRACT

This invention relates to fused thiophene acene compounds and their use in organic semiconductors. The compounds exhibit useful electronic properties such as high mobility and high on/off ratio. The compounds can be used in electronic devices such as field effect transistors (FETs), display devices, light-emitting diodes, photovoltaic cells, photo-detectors, and memory cells. Also provided are methods for making the fused thiophene acenes.

7 Claims, 2 Drawing Sheets

FUSED THIOPHENE ACENES AND ORGANIC SEMICONDUCTORS MADE THEREFROM

FIELD OF THE INVENTION

The present invention relates to a new class of fused thiophene acene compounds. The invention also relates to electronic devices and methods of manufacturing the electronic devices using the thiophene acenes.

BACKGROUND

Organic materials have been widely used in electronic devices such as organic field-effect transistors (OFETs), light emitting diodes (OLEDs), photovoltaic diodes, and liquid crystal displays. OFETs are of special interest for use in low-cost integrated circuit (IC) technology suitable for applications such as smart cards, electronic tags, displays, and memory devices. In OFETs, the semiconductor layer consists of organic semiconductor materials including conjugated polymers and oligomers. Many organic materials possessing the required electronic properties for the electronic device applications have been synthesized.

Organic compounds that have been investigated for use as semiconductors include conjugated polymers such as regioregular poly(3-alkylthiophene)s; copolymers of polyfluorene-bithiophene; polyaromatic amine and polythiophene derivatives; fused aromatic compounds such as pentacene, tetracene and their derivatives; and conjugated oligomers such as oligothiophenes, fluorene-thiophene oligomers, and phenyl-thiophene oligomers.

The performance of most of the above organic semiconductors compounds suffers from either low charge mobility (ca. ~0.1 cm$^2$/Vs) or instability. For example, although pentacene possesses high charge mobility (about 0.1 to 2 cm$^2$/Vs), it also has a relatively low band gap (2.2 eV) and a high HOMO (highest occupied molecular orbital) energy level, and is easily oxidized. Pentacene compounds often show high oxygen and humidity sensitivity, and therefore high on/off ratios can only be obtained in an inert atmosphere. These characteristics result in poor device stability and make pentacene compounds unsuitable for practical electronic circuit applications. On the other hand, compounds such as oligofluorenes, oligofluorene-thiophenes, phenylene-thiophene, and conjugated polyfluorene-thiophene polymers show improved stability, but their low charge mobility limits their applications in high efficiency electronic devices.

Therefore, there still exists a need for organic compounds that have high charge mobility and high on/off ratio, and that are stable to heat, light, and air. There is also a need for organic compounds that can be readily incorporated into electronic devices using commercially viable fabrication methods.

SUMMARY OF THE INVENTION

One embodiment of the invention is a compound represented by Formula 1:

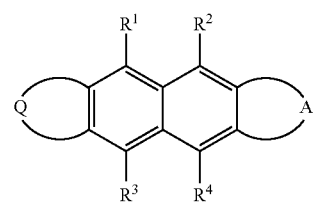

Formula 1 wherein
A and Q are independently selected from

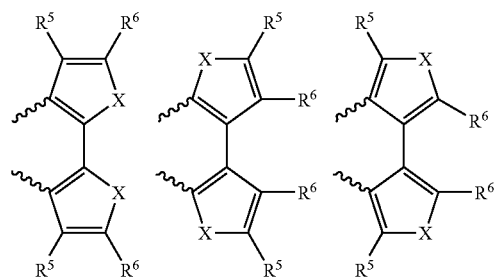

and each X is independently selected from the group consisting of S, O, SO, SO$_2$, Se, Te, NR, BR, PR, PO, PO$_2$, and SiR$_2$;
R$^1$-R$^6$ are selected independently from the group consisting of: hydrogen; substituted or unsubstituted alkyl; substituted or unsubstituted aryl; substituted or unsubstituted heteroaryl; halogen; hydroxy; substituted or unsubstituted aryloxy; substituted or unsubstituted alkoxy; substituted or unsubstituted alkenyl; substituted or unsubstituted alkynyl; substituted or unsubstituted amino; substituted or unsubstituted alkylthio; substituted or unsubstituted phosphino; substituted or unsubstituted silyl; —COR; —COOR; —PO$_3$R$_2$; —OPO$_3$R$_2$; —NC; —C$_n$F$_{2n+1}$; and —C$_n$F$_{2n+1}$C$_m$H$_{2m+1}$;
R is selected from the group consisting of hydrogen; substituted or unsubstituted alkyl; substituted or unsubstituted aryl; substituted or unsubstituted heteroaryl; substituted or unsubstituted alkenyl; substituted or unsubstituted alkynyl; and substituted or unsubstituted amino;
the substituents on substituted R and R$^1$ through R$^8$ are functional groups selected independently from the group consisting of cyanide; nitro; ester groups; ether groups; halogen; hydroxy; substituted or unsubstituted alkyl groups; substituted or unsubstituted aryl groups; and substituted or unsubstituted alkoxy groups; and
wherein any two adjacent groups selected from R$^1$-R$^6$ can be taken together to form a ring.

One embodiment provides electronic devices that comprise organic field-effect transistors (OFETs) that comprise the compositions represented by Formula 1. Also provided are methods for manufacturing OFETs using the compositions represented by Formula 1.

Another embodiment provides display devices comprising the compositions represented by Formula 1.

Yet another embodiment provides light-emitting diodes, photo conductors, memory cells, current limiters, field-effect diodes, Schottky diodes, photovoltaic cells, photo-detectors, thin film transistors (TFTs), rectifiers, transistors, thermistors and p-n junctions comprising the compositions represented by Formula 1.

DETAILED DESCRIPTION OF THE INVENTION

Figure 1A:
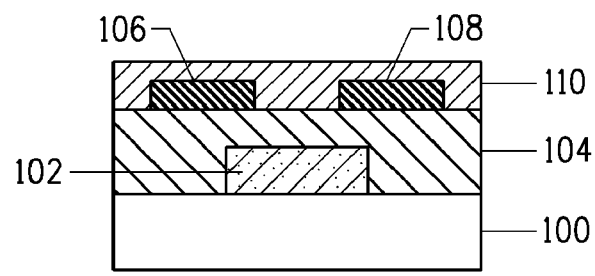
FIGS. 1A and 1B are schematic diagrams of the bottom contact mode and top contact mode, respectively, of an organic field effect transistor (OFET), in accordance with one embodiment of the invention.

This invention provides a new class of substituted tetracenes and a method for synthesizing these compounds. The invention also relates to organic semiconductor devices incorporating these and other substituted tetracenes.

The tetracenes are represented by Formula 1

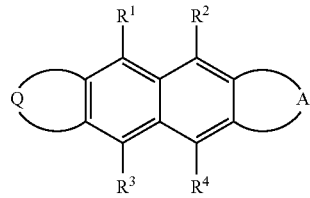

Formula 1 wherein
A and Q are independently selected from:

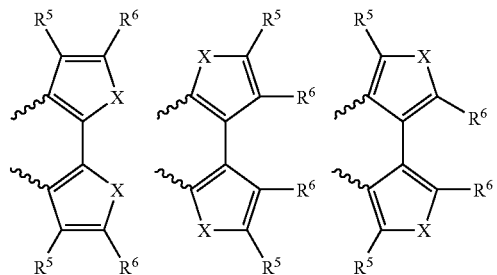

and each X is independently selected from the group consisting of S, O, SO, SO$_2$, Se, Te, NR, BR, PR, PO, PO$_2$, and SiR$_2$; R$^1$-R$^6$ are selected independently from the group consisting of hydrogen; substituted or unsubstituted alkyl; substituted or unsubstituted aryl; substituted or unsubstituted heteroaryl; halogen; hydroxy; substituted or unsubstituted aryloxy; substituted or unsubstituted alkoxy; substituted or unsubstituted alkenyl; substituted or unsubstituted alkynyl; substituted or unsubstituted amino; substituted or unsubstituted alkylthio; substituted or unsubstituted phosphino; substituted or unsubstituted silyl; —COR; —COOR; —PO$_3$R$_2$; —OPO$_3$R$_2$; —NC; —C$_n$F$_{2n+1}$; and —C$_n$F$_{2n+1}$C$_m$H$_{2m+1}$;
R is selected from the group consisting of hydrogen; substituted or unsubstituted alkyl; substituted or unsubstituted aryl; substituted or unsubstituted heteroaryl; substituted or unsubstituted alkenyl; substituted or unsubstituted alkynyl; and substituted or unsubstituted amino;
the substituents on substituted R and R$^1$ through R$^8$ are functional groups selected independently from the group consisting of cyanide; nitro; ester groups; ether groups; halogen; hydroxy; substituted or unsubstituted alkyl groups; substituted or unsubstituted aryl groups; and substituted or unsubstituted alkoxy groups; and
wherein any two adjacent groups selected from R$^1$-R$^6$ can be taken together to form a ring.

In one embodiment, the tetracenes are selected from compounds represented by Formula 1A, Formula 1B or Formula 1C:

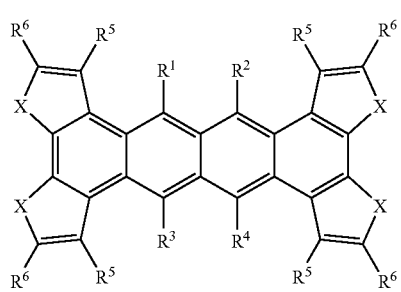

Formula 1A

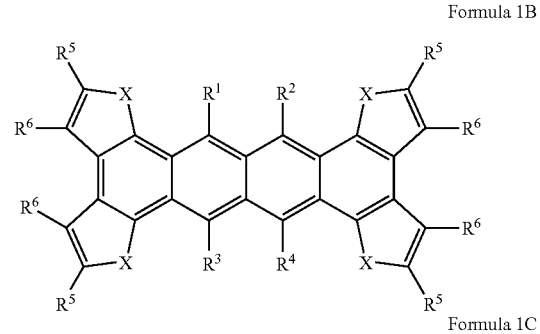

Formula 1B

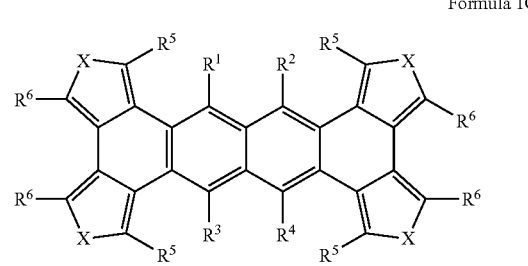

Formula 1C wherein each X and each of R$^1$-R$^6$ are independently selected and defined as above. In Formula 1A, "adjacent R groups" refers to (R$^1$, R$^2$), (R$^1$, R$^5$), (R$^5$, R$^6$), etc. In Formula 1B, "adjacent R groups" refers to (R$^1$, R$^2$), (R$^5$, R$^6$), (R$^6$, R$^6$), etc. In Formula 1C, "adjacent R groups" refers to (R$^1$, R$^2$), (R$^1$, R$^5$), (R$^6$, R$^6$), etc.

The term 'acene' as used herein refers to a hydrocarbon parent component that contains two or more ortho-fused benzene rings in a straight linear arrangement. 'Acenes' include naphthalene (two ortho-fused benzene rings) and anthracene (three ortho-fused benzene rings). Systems of four or more fused benzene rings are named from the numerical prefix denoting the number of benzene rings followed by the ending '-acene'. 'Tetracene' comprises four ortho-fused benzene rings.

The term 'alkyl' or 'unsubstituted alkyl', whether as part of another term or used independently, denotes a saturated hydrocarbon radical. Examples of alkyl groups include n-butyl, n-pentyl, n-heptyl, iso-butyl, t-butyl, and iso-pentyl. The term 'substituted alkyl' denotes alkyl that is mono- or poly-substituted with the same or different substituent groups.

The term 'alkenyl' or 'unsubstituted alkenyl', whether as part of another term or used independently, denotes hydrocarbon radicals having one or more double bonds between neighboring carbon atoms of the radical. Examples of alkenyl groups include vinyl, allyl, butenyl, pentenyl, and heptenyl. The term 'substituted alkenyl' denotes an alkenyl group that is mono- or poly-substituted with the same or different substituent groups.

The term 'alkynyl' or 'unsubstituted alkynyl', whether as part of another term or used independently, denotes hydrocarbon radicals having one or more triple bonds between neighboring carbon atoms of the radical. Examples of alkynyl groups include ethynyl, propynyl, butynyl, hexynyl and heptynyl. The term 'substituted alkynyl' denotes an alkynyl group that is mono- or poly-substituted with the same or different substituent groups.

Suitable substituent groups include cyanide groups, nitro groups, ester groups, ether groups, halogen substituents, hydroxy groups, substituted or unsubstituted alkyl groups, substituted or unsubstituted aryl groups, and substituted or unsubstituted alkoxy groups. Preferred substituents include ether groups and fluorine substituents.

Substituted and unsubstituted alkyl groups, alkenyl groups, and alkynyl groups can be straight-chain or branched-chain. Examples of straight-chain alkyls, alkenyls, and alkynyls include n-butyl, n-pentyl, n-heptyl, n-octyl, n-butenyl, n-pentenyl, n-heptenyl, and n-heptynyl. Examples of branched-chain alkyls, alkenyls, and alkynyls include iso-butyl, t-butyl, iso-pentyl, neo-pentyl, isopentenyl, and neopentenyl.

Although not wanting to be bound by theory, it is believed that certain geometric characteristics of the substituted acenes correlate with their performance in electronic devices. Since the band gaps of these semiconductors are relatively large (ca. ~2.3-3.5 eV), the compounds are also highly stable materials.

Compounds represented by Formula 1 that have a twisted acene nucleus are better suited than those with a flat acene nucleus for use in OLEDs. The twisting of the acene group is largely controlled by the steric interactions of the substituents on the acene ring. The compounds of Formula 1 exhibit high charge mobilities and high on/off ratios and are suitable for use in the fabrication of semiconductor devices. These compounds have high thermal stability and are unaffected by light or air so that semiconductor devices do not need to be fabricated in an inert atmosphere. The use of these compounds also allows the manufacture of electronic devices at a low substrate temperature. In addition, these compounds have good film-forming abilities.

Preferably, $R^1$-$R^6$ are H, F or —CN for tetracenes used in OFETs. Examples of tetracenes represented by Formula 1 include Compounds 1-30:

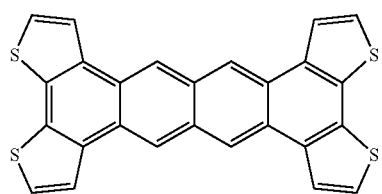

Compound 1

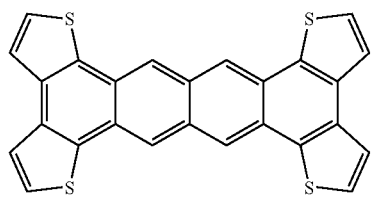

Compound 2

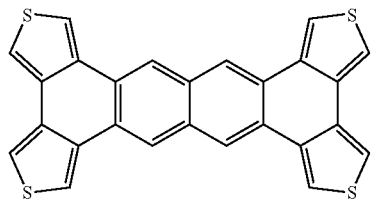

Compound 3

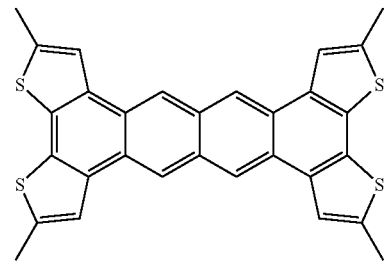

Compound 4

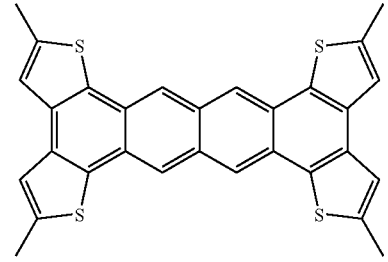

Compound 5

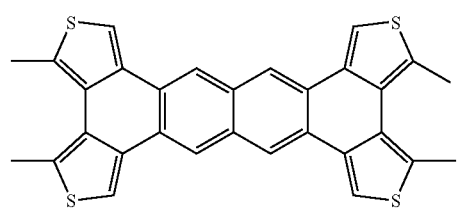

Compound 6

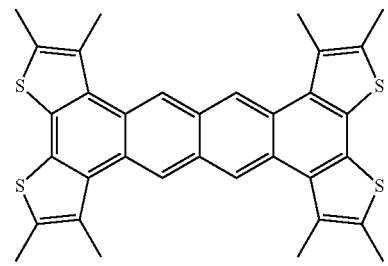

Compound 7

-continued
Compound 8
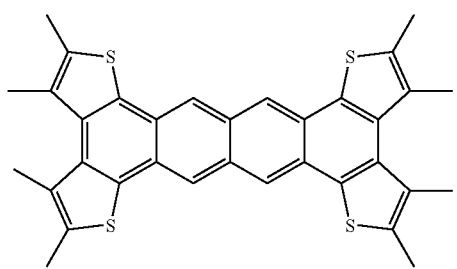
Compound 9
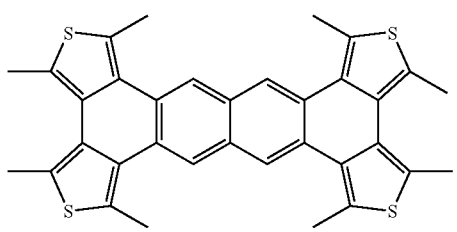
Compound 10
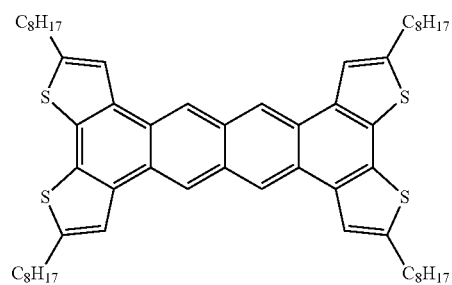
Compound 11
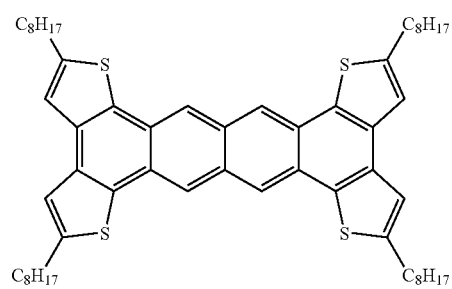
Compound 12
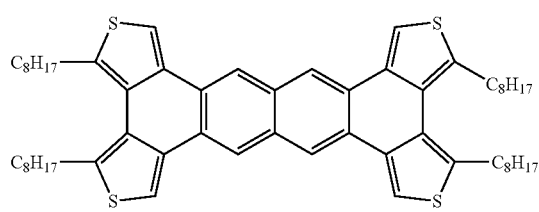
-continued
Compound 13
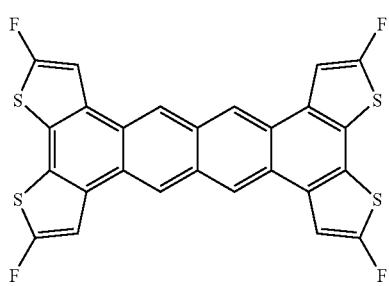
Compound 14
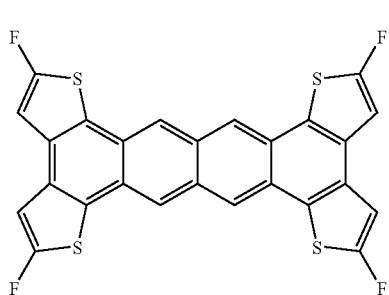
Compound 15
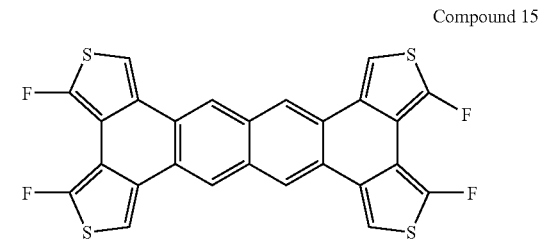
Compound 16
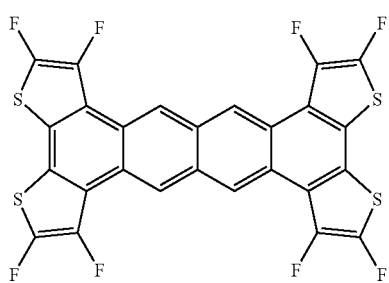
Compound 17
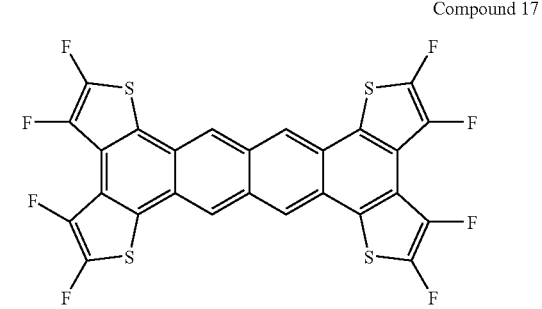

Compound 18
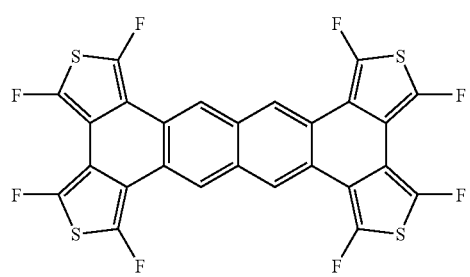
Compound 19
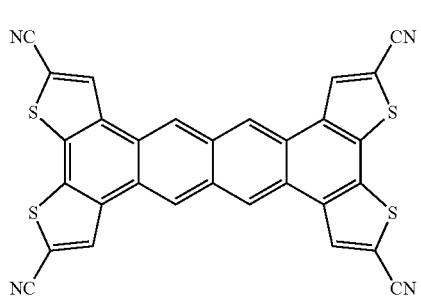
Compound 20
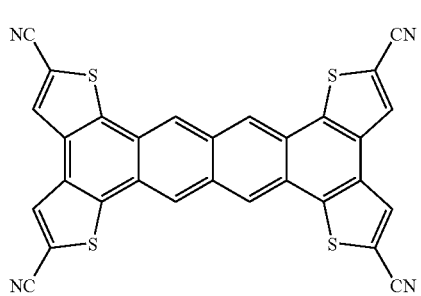
Compound 21
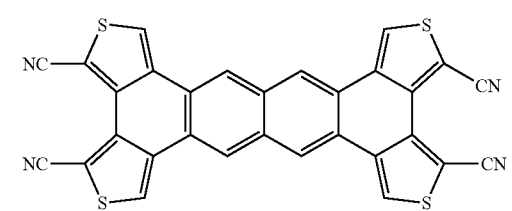
Compound 22
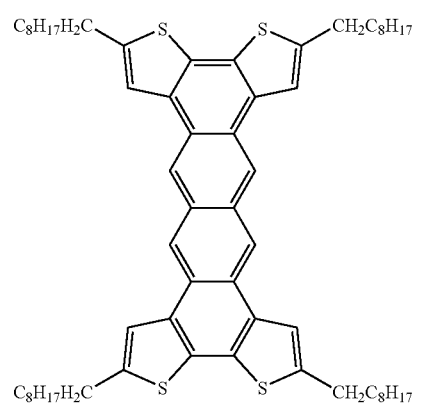
Compound 23
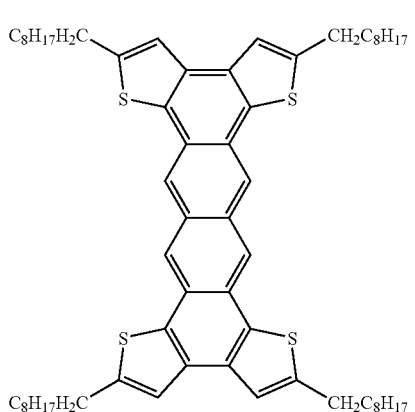
Compound 24
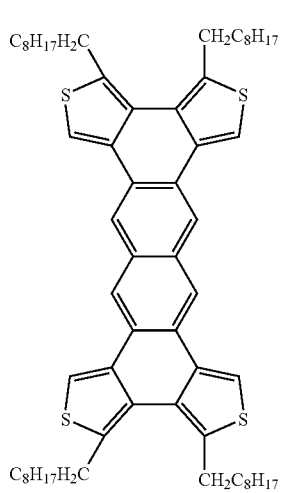
Compound 25
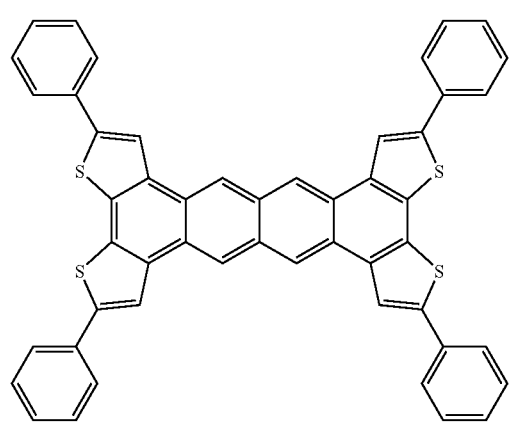

-continued

Compound 26

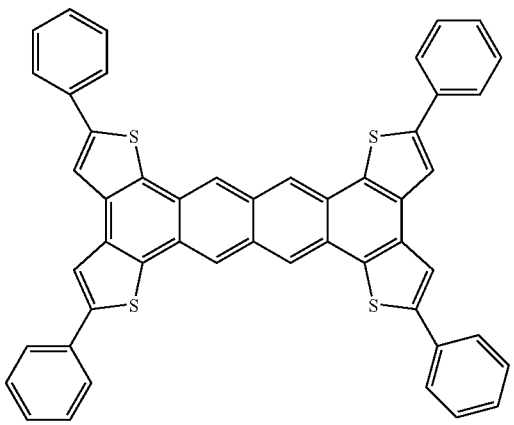

Compound 27

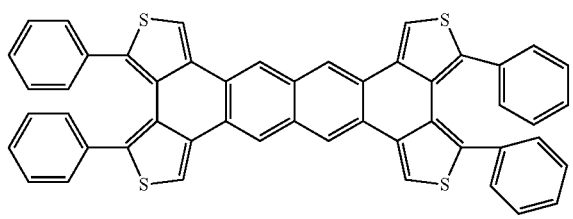

Compound 28

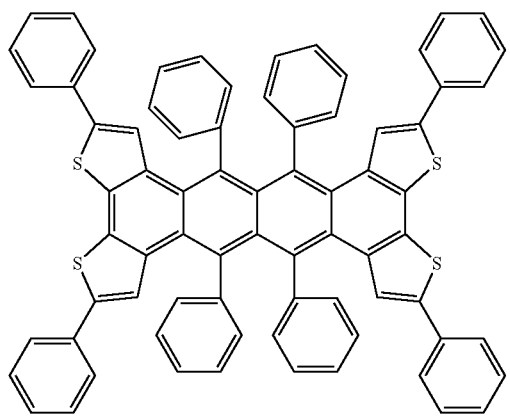

Compound 29

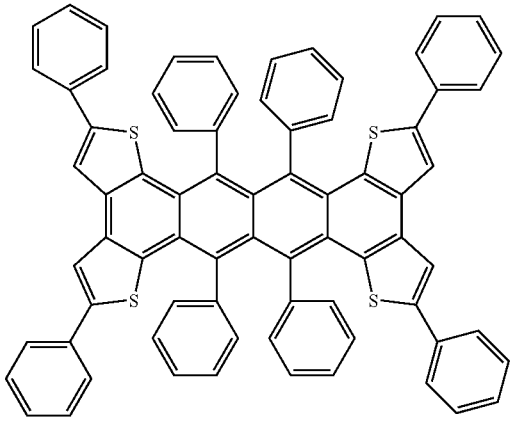

-continued

Compound 30

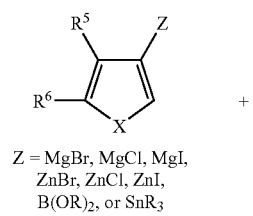

The compounds represented by Formula 1 can be prepared by the conjugated cross-coupling reaction of a substituted boronic acid (or ester) with a dihaloarylene. Such reactions are commonly referred to as "Suzuki couplings" and are illustrated in Schemes 1A/B-3A/B.

Scheme 1A Conjugated Coupling

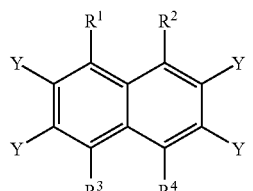

$Z$ = MgBr, MgCl, MgI,
ZnBr, ZnCl, ZnI,
B(OR)$_2$, or SnR$_3$

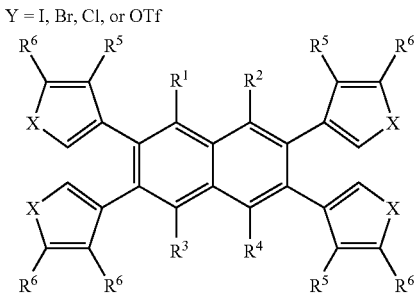

$Y$ = I, Br, Cl, or OTf

Scheme 1B Ring Closing Reaction

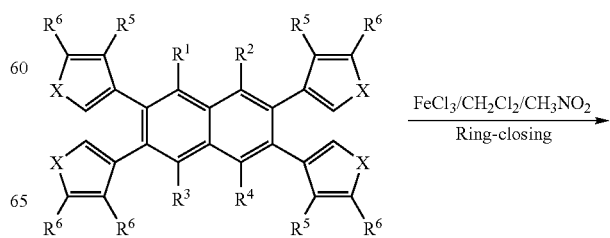

$\xrightarrow{\text{FeCl}_3/\text{CH}_2\text{Cl}_2/\text{CH}_3\text{NO}_2}{\text{Ring-closing}}$ -continued
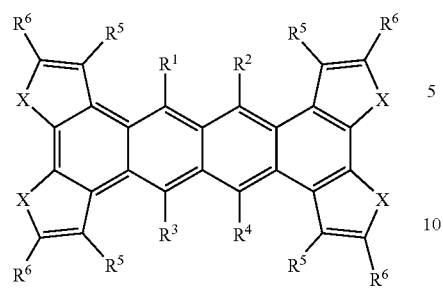
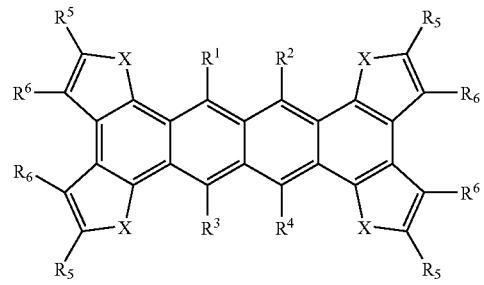
Scheme 2A Conjugated Coupling
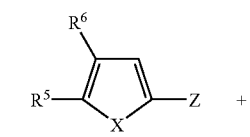
Z = MgBr, MgCl, MgI,
ZnBr, ZnCl, ZnI,
B(OR)$_2$, or SnR$_3$
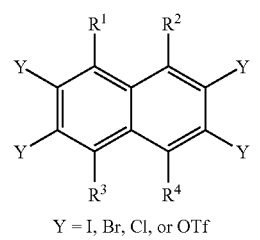
Y = I, Br, Cl, or OTf
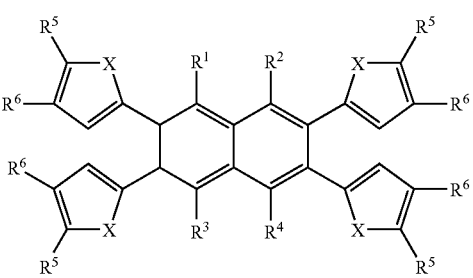
Scheme 2B Ring Closing Reaction
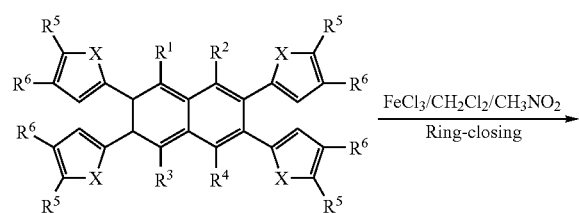
Scheme 3A Conjugated Coupling
Z = MgBr, MgCl, MgI,
ZnBr, ZnCl, ZnI,
B(OR)$_2$, or SnR$_3$
Y = I, Br, Cl, or OTf
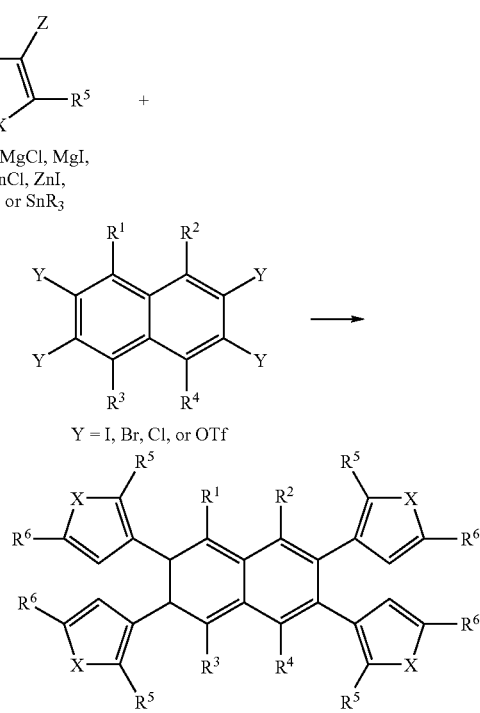
Scheme 3B Ring Closing Reaction
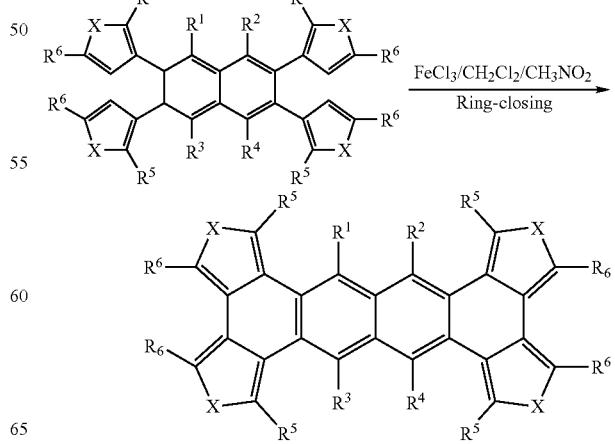

The reagents are not restricted to the above substituted boronic acids or esters. Any Suzuki-coupling reagents used as organoboronic coupling reagents can be used, such as potassium trifluoro(organo)borates. (Darses, S.; Genet, J. P., Eur. J. of Org. Chem. (2003), (22), 4313-4327.). The reaction conditions, catalysts, solvents, phase transfer agents, and reaction media can also be varied, as described by W. A. Herrmann, et al., "C—C coupling reactions (Heck, Stille, Suzuki, etc.). Aqueous-Phase Organometallic Catalysis" (2nd Edition) (2004), 511-523.)

The tetra-substituted naphthalenes of Schemes 1A, 2A and 3A (where Y=Cl, Br, I or OTf) can be synthesized according to Scheme 4, as described in the Journal of Porphyrins and Phthalocyanines, Vol. 1, 77-86 (1997).

Scheme 4

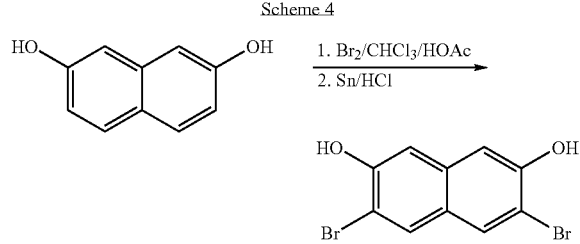

Semiconductor devices have been described by S. M. Sze in Physics of Semiconductor Devices, 2nd edition, John Wiley and Sons, New York (1981). Such devices include rectifiers, transistors (of which there are many types, including p-n-p, n-p-n, and thin-film transistors), current limiters, thermistors, p-n junctions, field-effect diodes, Schottky diodes, and so forth. Semiconductor devices can be prepared or manufactured by known methods (Peter Van Zant, Microchip Fabrication, Fourth Edition, McGraw-Hill, New York (2000)). In each semiconductor device, the semiconductor material is combined with one or more metals or insulators to form the device. Common to all semiconductor devices is the presence of one or more semiconductor materials. The compounds represented by Formula 1 can be used as the semiconductor material in semiconductor devices.

A particularly useful type of transistor device, the thin-film transistor (TFT), generally includes a gate electrode, a gate dielectric on the gate electrode, a source electrode and a drain electrode adjacent to the gate dielectric, and a semiconductor layer adjacent to the gate dielectric and adjacent to the source and drain electrodes (see, for example, S. M. Sze, supra, page 492). These components can be assembled in a variety of configurations. More specifically, an organic thin-film transistor (OTFT) has an organic semiconductor layer.

Typically, a substrate supports the OTFT during manufacturing, testing, and/or use. Optionally, the substrate can provide an electrical function for the OTFT. Useful substrate materials include organic and inorganic materials. For example, the substrate can comprise inorganic glasses, ceramic foils, polymeric materials (e.g., acrylics; epoxies; polyamides; polycarbonates; polyimides; polyketones; poly(oxy-1,4-phenyleneoxy-1,4-phenylenecarbonyl-1,4-phenylene), sometimes referred to as poly(ether ether ketone) or PEEK; polynorbornenes; polyphenyleneoxides; poly(ethylene naphthalenedicarboxylate) (PEN); poly(ethylene terephthalate) (PET); poly(phenylene sulfide) (PPS)). The substrate can also comprise filled polymeric materials (for example, fiber-reinforced plastics (FRP)), or coated metallic foils.

The gate electrode can be any useful conductive material. For example, the gate electrode can comprise doped silicon or a metal (e.g., aluminum, chromium, gold, silver, nickel, palladium, platinum, tantalum, or titanium). Conductive polymers also can be used, for example polyaniline or poly(3,4-ethylenedioxythiophene)/poly(styrene sulfonate) (PEDOT:PSS). In addition, alloys, combinations, and multilayers of these materials can be used. In some OTFTs, a single material can function as the gate electrode function and the substrate. For example, doped silicon can function as the gate electrode and also support the OTFT.

The gate dielectric generally covers the gate electrode. The gate dielectric electrically insulates the gate electrode from the balance of the OTFT device. Useful materials for the gate dielectric can comprise any inorganic electrically insulating material (e.g., strontiates, tantalates, titanates, zirconates, aluminum oxides, silicon oxides, tantalum oxides, titanium oxides, silicon nitrides, barium titanate, barium strontium titanate, barium zirconate titanate, zinc selenide, or zinc sulfide). In addition, alloys, combinations, and multilayers of these materials can be used for the gate dielectric.

The source and drain electrodes are separated from the gate electrode by the gate dielectric, while the organic semiconductor layer can be over or under the source and drain electrodes. The source and drain electrodes can be any sufficiently conductive material (e.g., metals such as aluminum, barium, calcium, chromium, gold, silver, nickel, palladium, platinum, titanium, or alloys thereof). Conductive polymers such as polyaniline, PEDOT:PSS, as well as combinations and multilayers thereof can also be used a source and drain electrodes. Some of these materials are appropriate for use with n-type semiconductor materials and others are appropriate for use with p-type semiconductor materials, as is known in the art.

In a printed OFET array, a silver layer or a conducting polymer layer such as polyaniline (PANI) with dispersed carbon nanotubes (PANI/NT) can be applied as a patterned gate electrode, which can be thermal transfer printed using a CREO-Trendsetter TML printer by using a silver-coated donor sheet or a polyaniline-carbon nanotube (PANI/NT) composition as donor and a receiver sheet comprising polyester and/or poly(ethylene/vinyl acetate). Suitable polyesters include PET (polyethylene terephthalate) and PEN (polyethylene naphthalate). Suitable commercially available films for use as receiver sheets include Mylar®-RS 8, available from DuPont Teijin Films, Hopewell, Va. A dielectric layer of latex can then be laminated or thermal printed over the patterned gate. The source and drain patterns can be printed, for example, using a CREO-Trendsetter TML printer by using a polyaniline-carbon nanotube (PANI/NT) composition as donor and a Mylar® RS 8 receiver sheet. Semiconductors can then be thermally evaporated on top of the source and drain electrodes through a shadow mask. The performance of the transistors in the arrays can be evaluated after the PANI/NA gate or silver gate layer, dielectric layer, and PANI/NT source/drain electrode layers and the semiconductor layer are assembled.

The thin film electrodes (i.e., the gate, source, and drain electrodes) can be provided by any of several means, including physical vapor deposition (e.g., thermal evaporation or sputtering) and ink jet printing. The patterning of these electrodes can be accomplished by known methods such as shadow masking, additive photolithography, subtractive photolithography, printing, microcontact printing, or pattern coating.

Figure 1B:
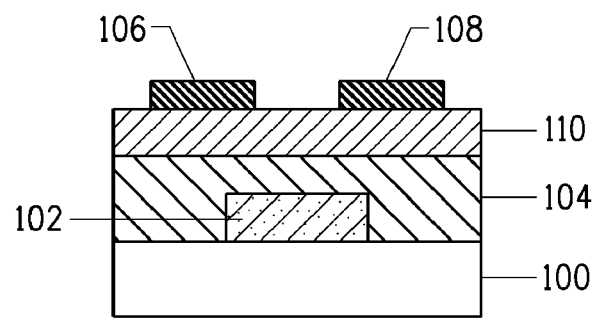

FIGS. 1A and 1B are schematic diagrams of the bottom contact mode and top contact mode, respectively, of an organic field effect transistor (OFET), as one example of a TFT. A TFT typically comprises a substrate, e.g., an n-type silicon wafer. The wafer functions as the gate electrode for the TFT device. A dielectric layer 104 of silicon dioxide is typically thermally grown on the gate electrode.

For the bottom-contact mode OFET (FIG. 1A), electrodes 106 and 108, which form channels for the source and drain, respectively, can be created on the silicon dioxide layer using a photolithographic process. A semiconductor layer 110 is then deposited over the surface of electrodes 106 and 108 and dielectric layer 104.

For the top-contact mode OFET (FIG. 1B), semiconductor layer 110 is deposited on dielectric layer 104 before the fabrication of electrodes 106 and 108. FIG. 1B is a schematic diagram of an OFET showing the relative positions of the active layers of such a device in top contact mode.

Figure 1C:
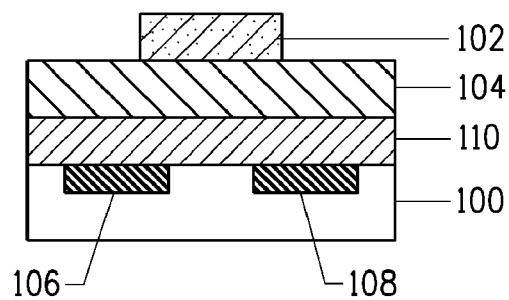
FIGS. 1C and 1D are schematic diagrams of the bottom contact mode and top contact mode, respectively, of an organic field effect transistor (OFET) with the gate at the top.

FIG. 1C is a schematic diagram of an OFET showing the relative positions of the active layers of such a device in bottom-contact mode with the gate at the top.

Figure 1D:
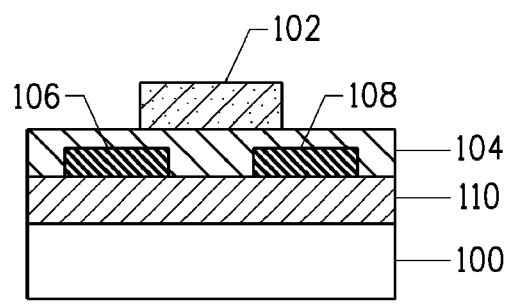

FIG. 1D is a schematic diagram of an OFET showing the relative positions of the active layers of such a device in bottom contact mode with the gate at the top.

In the devices made from the substituted acenes disclosed herein, semiconductor layer 110 comprises one or more compounds represented by Formula 1. Semiconductor layer 110 may be deposited by various techniques known in the art, such as thermal evaporation, chemical vapor deposition, thermal transfer, ink-jet printing, and screen-printing. Useful dispersion thin film coating techniques for deposition include spin coating, doctor blade coating, and drop casting.

The semiconductor compounds can also be used in other OFET device configurations, e.g., gate-top device configurations. U.S. Pat. No. 6,621,098 describes such device structures.

In some cases the substrate 100 can be a plastic polymer material, inorganic insulator or metal substrate. The gate electrode 102 can be coated onto the substrate by various coating methods such as spin coating, bar coating, and doctor blade coating, or printing methods such as thermal laser printing, inkjet printing, and screen printing.

Display Devices

Figure 2:
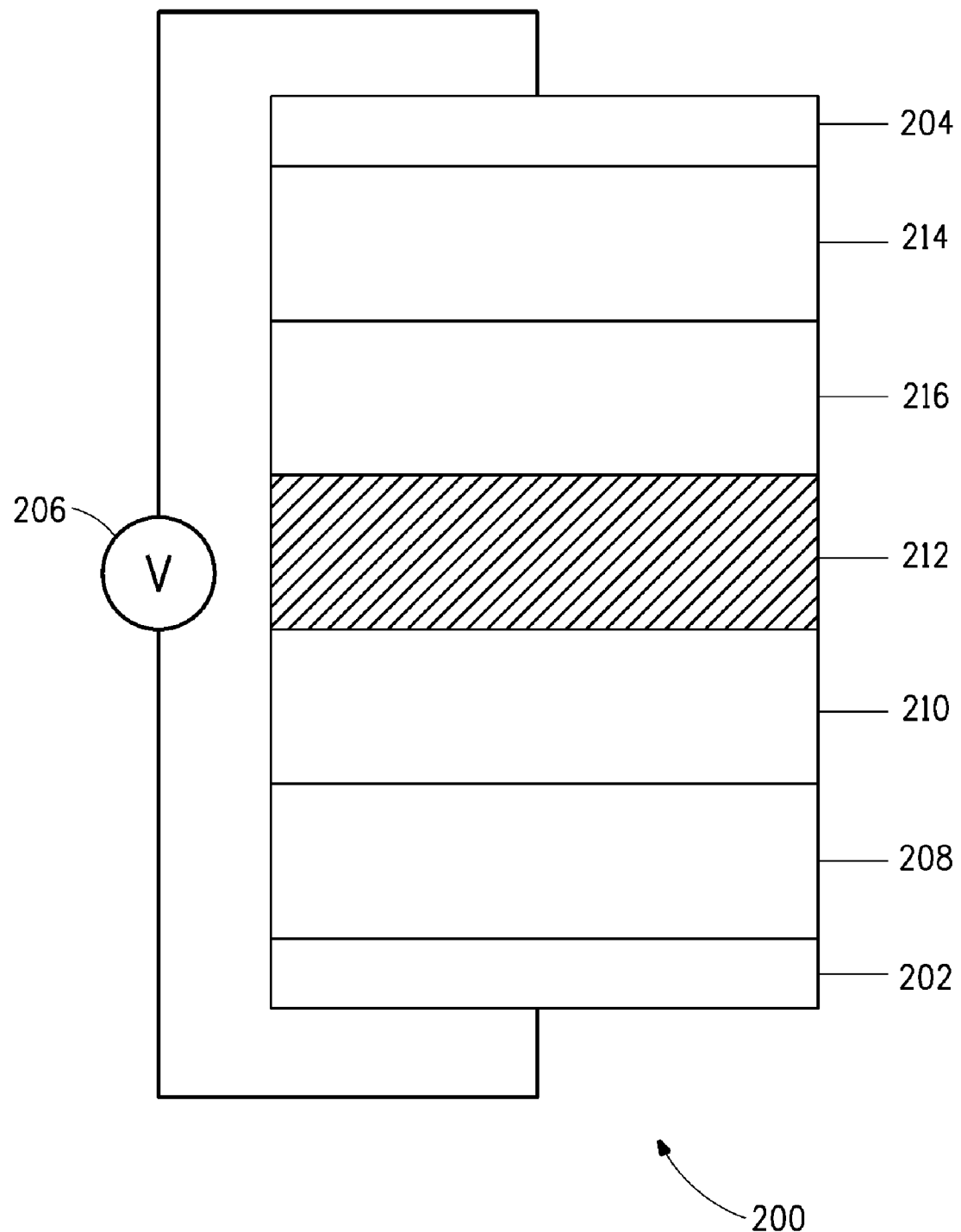
FIG. 2 is a schematic representation of a display device, in accordance with one embodiment of the invention.

FIG. 2 is a schematic representation of a display device 200, in accordance with one embodiment of the invention. An anode 202 and a cathode 204 are electrically connected to an electric power supply 206. Electric power supply 206 is preferably a current source. A hole-injecting layer 208 is present in contact with anode 202. Hole injecting layer 208 facilitates the injection of holes from anode 202 into display device 200. A hole-transporting layer 210 is present in contact with hole injecting layer 208 from one side and an organic semiconductor layer 212 on the other side. Hole-transporting layer 210 facilitates the passage of holes from hole-injecting layer 208 to organic semiconductor layer 212.

Similarly, an electron-injecting layer 214 is present in contact with cathode 204. Electron-injecting layer 214 facilitates the injection of electrons from cathode 204 into display device 200. An electron-transporting layer 216 is present in contact with electron-injecting layer 214 from one side and organic semiconductor layer 212 on the other side. Electron-transporting layer 216 facilitates the passage of electrons from electron-injecting layer 214 to organic semiconductor layer 212. Organic semiconductor layer 212 comprises one or more compounds represented by Formula 1.

When electric current is applied to anode 202 and cathode 204, electrons and holes are injected into device 200. These electrons and holes combine in organic semiconductor layer 212 and emit light photons due to the electroluminescent properties of the compounds present in organic semiconductor layer 212.

Characterization of FET devices by determination of threshold voltages and on/off ratios can be accomplished by methods known in the art.

While the preferred embodiments of the invention have been illustrated and described, it will be clear that the invention is not limited to these embodiments only. Numerous modifications, changes, variations, substitutions, and equivalents will be apparent to those skilled in the art without departing from the spirit and scope of the invention as described in the claims.

EXAMPLES

The present invention is further illustrated in the following Examples. These Examples, while indicating preferred embodiments of the invention, are given by way of illustration only.

General

Thermo-gravimetric analysis (TGA) was carried out on a TA Instruments Q550 TGA System™ at a heating rate of 10° C./min and at a nitrogen flow rate of 60 cm$^3$/min.

Cyclic voltammetry (CV) was performed on an EG&G Parc Model 273A™ potentiostat/galvanostat system with a three-electrode cell in a solution of $Bu_4NBF_4$ (0.1 M) in acetonitrile at a scan rate of 50 mV/s.

The semiconductor films were coated on a disc Pt electrode (0.050 cm$^2$) by vacuum sublimation. A Pt wire was used as the counter electrode and an Ag/AgNO$_3$ (0.01M) electrode was used as the reference electrode. Prior to each series of measurements, the cell was deoxygenated with argon. Organic semiconductor was added to the electrolyte solution (0.2 mg/mL). A Pt wire was used as the counter electrode and an Ag wire electrode was used as the reference electrode. The electrode's potential was calibrated with the saturated calomel electrode (SCE) by measuring the ferrocene/ferrocenium couple in this system (0.15 V versus SCE). The band gaps were derived from the difference between onset potentials.

X-ray data were taken on a CAD-4 diffractometer with copper Kα radiation, and the structure was solved using the NRCVAX™ suite of programs.

Nuclear magnetic resonance (NMR) spectra were taken on a Bruker™ 500 MHz spectrometer. All chemical shifts were reported relative to tetramethylsilane (TMS) at 0.0 ppm, unless otherwise stated.

2,6-Dibromoanthracene was synthesized according to the method of Hodge, P.; Power, G. A.; Rabjohns, M. A. *Chem. Commun.* 1997, 73.

Example 1

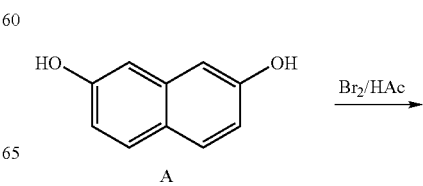

A

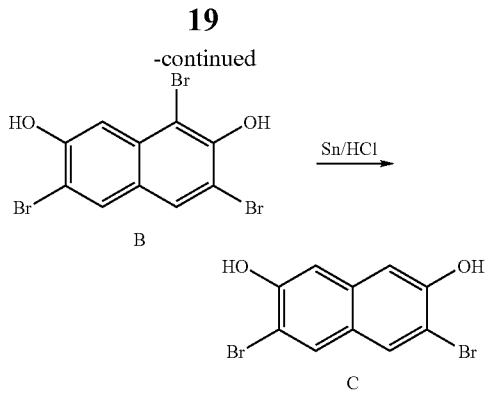

Into a 500 mL round bottom flask, bromine (128 g, 0.8 mole) in acetic acid (200 mL) was added slowly over 0.5 h at room temperature to a solution of 2,7-dihydronaphthalene (32.0 g, 0.2 mole) dissolved in acetic acid (300 mL). An orange yellow precipitate was formed. This was stirred at 80° C. for 1 h. Then water (100 mL) was added, and the light yellow mixture was heated at 80° C. for an additional hour. Tin powder (48 g, 0.4 mol) was added in three portions (over about 10 min) and the mixture heated to reflux at 80° C. An off-white precipitate was formed. After 1 h, a light yellow clear solution was obtained. TLC (hexane:ethyl acetate=1:1) showed several products (Rf: 0.7, 0.65, 0.6 and 0.5 and 0.4). Rf=0.5 is the main product. Reflux was continued overnight until all the tin disappeared. Most of the solvent was evaporated and the residue was poured into water. The precipitate was collected by filtration. The solid was dissolved in ethyl acetate and the solvent was partially evaporated until a white powder was formed. This was repeated several times, and a white powder was collected (Rf=0.03). Flash column chromatography using hexane:ethyl acetate (2:1) was run, discarding the first small part, then collecting the main point to give a light brown powder of intermediate compound C. (Yield 66%, 42 g). $C_{10}H_6Br_2O_2$: EI, MS m/z (%): 318 (100, $M^+$).

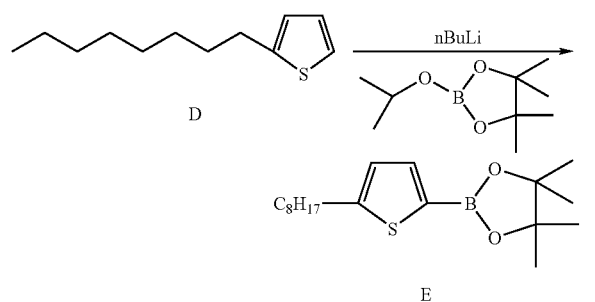

Into a solution of compound D (19.6 g, 0.10 mole) and anhydrous ether (200 mL), n-BuLi (1.6 M in hexane, 75 mL) was added dropwise at room temperature. After addition, the reaction mixture was stirred at reflux for 1 h, giving an orange solution. The solution was cooled to −78° C., then dioxaborolane (22 g, 0.13 mol) was added and the mixture was stirred for about 2 h. The mixture was extracted with water (1×). The organic layer was dried over anhydrous magnesium sulfate and filtered. The filtrate was concentrated on a rotary evaporator. The residue was submitted to column chromatography, eluent:hexane=1:3 (Rf1=0.45, rf2=0.4, rf3=0.1). Flash column chromatography using hexane:ethyl acetate=1:5 with 1% $Et_3N$ additive produced a colorless liquid of intermediate compound E. 29.1 g, (yield 90%). $C_{18}H_{31}BO_2S$: EI, MS m/z (%): 322 (100, $M^+$).

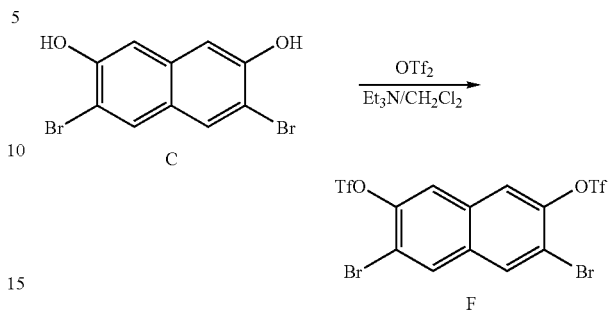

Intermediate compound C (6.36 g, 0.02 mole) was dissolved in dichloromethane (100 mL) and triethylamine (10 g, 0.1 mole), and the mixture was cooled to −10° C. Trifluoromethanesulfonic anhydride (17 g, 0.06 mol) dissolved in dichloromethane (25 mL) was then added dropwise over a period of 1 h. After complete addition, the reaction mixture was stirred for 1 h at −10° C. The mixture was allowed to warm to room temperature and stirred at this temperature for 15 h, after which the reaction was quenched by pouring into ice cold hydrochloric acid (5%). The layers were separated and the aqueous phase was extracted three times with dichloromethane. The combined organic layers were washed with saturated aqueous sodium hydrogen carbonate solution and brine and dried with $Na_2SO_4$, and the solvents were evaporated to dryness under reduced pressure. The resulting product was further purified by column chromatography on silica gel with hexane/ethyl acetate (5:1, v/v) as eluent (Rf=0.6, Rfst=0.02, Rfimpurity=0.3) to give a light-yellow powder of intermediate compound F, 8.1 g, yield 67%. $C_{12}H_4Br_2F_6O_6S_2$: EI, MS m/z (%): 582 (100, $M^+$).

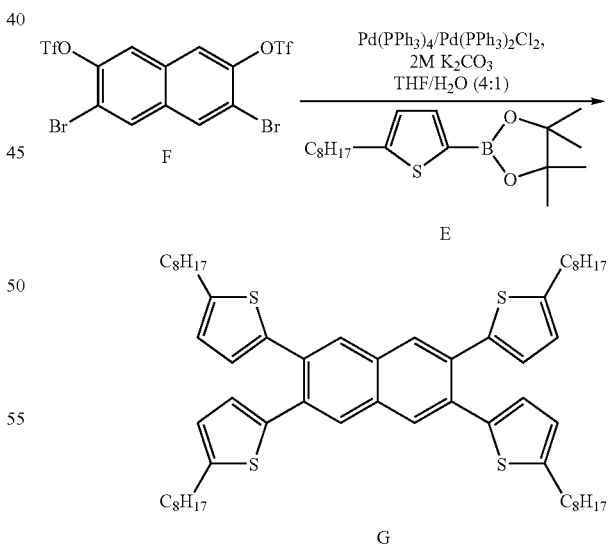

Into a 350 mL round bottom flask was added compound F (2.91 g, 0.005 mol), compound E (8.0 g, 0.025 mol), and then THF (200 mL). The mixture was purged with $N_2$ for 10 min. Then $K_2CO_3$ (11.0 g, 0.08 mole) dissolved in water (40 mL) was added. The mixture was purged with $N_2$ for 10 min. A catalytic amount of $Pd(PPh_3)_4$ (0.45 g) and $Pd(PPh_3)_2Cl_2$ (0.25 g) were added. The mixture was refluxed for 12 h. TLC (hexane) gave a blue spot (Rf 0.85) and a brown spot (Rf 0.9); the starting material (Rf=0.4, 0.6) had disappeared. Column chromatography using hexane as eluent gave a light yellow powder intermediate compound G (2.8 g, yield: 62%). $C_{58}H_{80}S_4$: EI, MS m/z (%): 904 (100, M+).

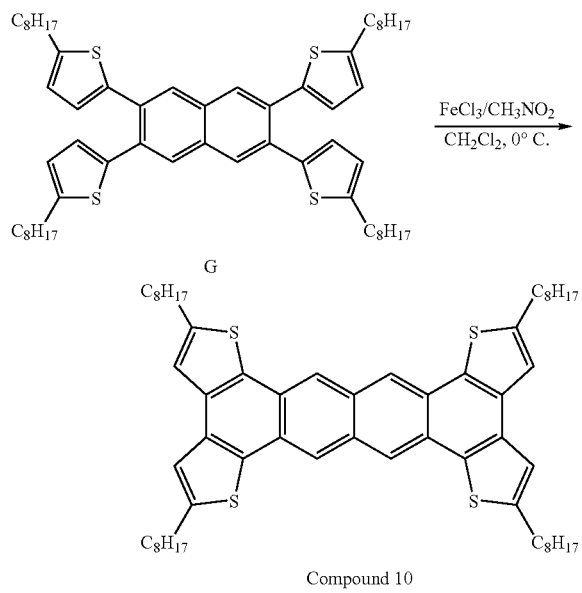

G

Compound 10

Into a 1 liter round bottom flask containing compound G dissolved in dry $CH_2Cl_2$ (770 mL) was added a solution of $FeCl_3$ (1.63 g, 10 mmol) in $CH_3NO_2$ (30 mL) at 0° C. After 30 min, the mixture was quenched with methanol and then stirred for 0.5 h. The mixture was filtered, and the solid was washed first with methanol, then three times with water (100 mL each). The filtered solid was washed with methanol and acetone, ether and then dried. Flash column chromatography using $CHCl_3$ was followed by recrystallization. An orange powder was collected (0.65 g, yield: 93%). $C_{58}H_{76}S_4$: EI, MS m/z (%): 900 (100, M+).

Example 2

Characterization of FET Devices

This Example summarizes results obtained for the characterization of FET devices that had a W/L ratio of 10, where W is the channel width and L is the channel length.

The FET devices were fabricated in a similar manner as described in conjunction with FIG. 1B. Thereafter, the performance of each FET device was characterized using an Agilent 4155C™ Semiconductor Parameter Analyzer interfaced with a probe station.

Measurements were made under ambient conditions, with no special precautions taken to control temperature, or to exclude light or air.

The results were obtained from the characterization of the OFET devices using compound 10 are summarized in the Table. These results show that solution processible OFET devices comprising compounds of Formula 1 have high mobilities and high on/off ratios.

TABLE

OFET Device Characteristics of Compound 10 using solution process

| SC Material | Substrate Temperature (Example) | $\mu^{sat}$ $\mu^{lin}$ (cm²/Vs) | On/Off$^{sat}$ On/Off$^{lin}$ | $V_t^{sat}$ $V_t^{lin}$ (V) | SubThrSW$^{sat}$ SubThrSW$^{lin}$ (V/decade) |
|---|---|---|---|---|---|
| Comp 10 | 24° C. | 0.018 ± 0.007 | 5.2 × 10⁵ | −14.2 | 3.10 |
|  |  | 0.011 ± 0.003 | 1.9 × 10⁶ | −13.0 | NA |
|  | 60° C. | 0.027 ± 0.006 | 7.5 × 10⁵ | −12.2 | 4.23 |
|  |  | 0.013 ± 0.008 | 6.4 × 10⁵ | −10.1 | NA |

What is claimed is:

1. An electronic device comprising one or more compounds represented by Formula 1:

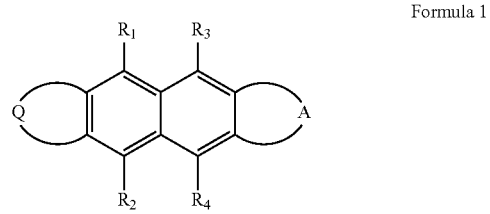

Formula 1 wherein
each A and Q are independently selected from the group consisting of

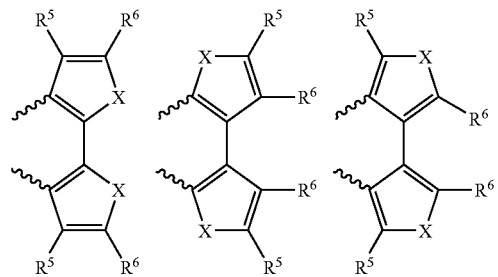

wherein each X is independently selected from the group consisting of S, O, SO, $SO_2$, Se, Te, NR, BR, PR, PO, $PO_2$, and $SiR_2$;

$R^1$-$R^6$ are selected independently from the group consisting of hydrogen; substituted or unsubstituted alkyl; substituted or unsubstituted aryl; substituted or unsubstituted heteroaryl; halogen; hydroxy; substituted or unsubstituted aryloxy; substituted or unsubstituted alkoxy; substituted or unsubstituted alkenyl; substituted or unsubstituted alkynyl; substituted or unsubstituted amino; substituted or unsubstituted alkylthio; substituted or unsubstituted phosphino; substituted or unsubstituted silyl; —COR; —COOR; —PO₃R₂; —OPO₃R₂; —NC; —$C_nF_{2n+1}$; and —$C_nF_{2n+1}C_mH_{2m+1}$;

R is selected from the group consisting of hydrogen; substituted or unsubstituted alkyl; substituted or unsubstituted aryl; substituted or unsubstituted heteroaryl; substituted or unsubstituted alkenyl; substituted or unsubstituted alkynyl; and substituted or unsubstituted amino;

the substituents on substituted R and $R^1$ through $R^6$ are functional groups selected independently from the group consisting of cyanide; nitro; ester groups; ether groups; halogen; hydroxy; substituted or unsubstituted alkyl groups; substituted or unsubstituted aryl groups; and substituted or unsubstituted alkoxy groups.

2. The electronic device of claim 1, wherein the device is a thin film transistor, a field effect transistor, a light-emitting diode, a photo conductor, a memory cell, a current limiter, a field-effect diode, a Schottky diode, a photovoltaic cell, a photo-detector, a rectifier, a thermistor or a p-n junction comprising the compositions represented by Formula 1.

3. The electronic device of claim 1 wherein the compound is selected from the group consisting of Compounds 1-30:

Compound 1

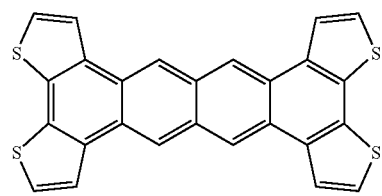

Compound 2

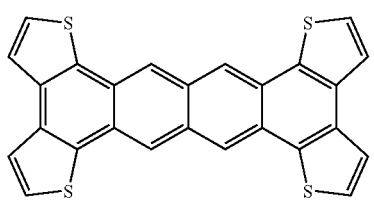

Compound 3

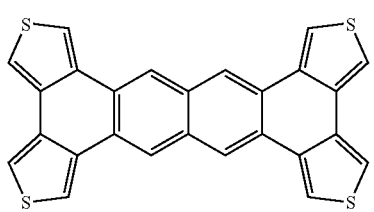

Compound 4

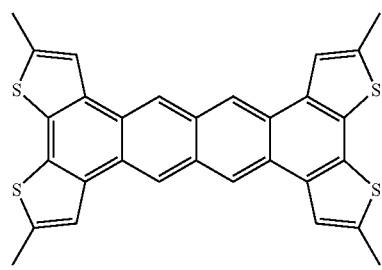

Compound 5

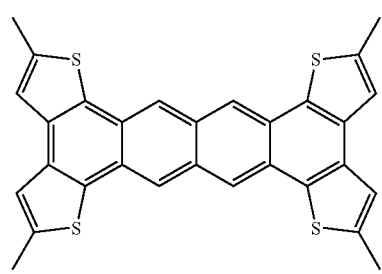

-continued

Compound 6

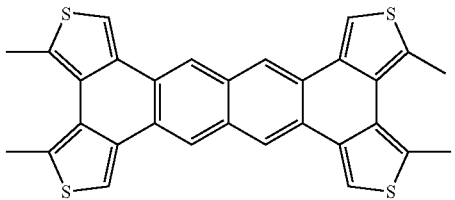

Compound 7

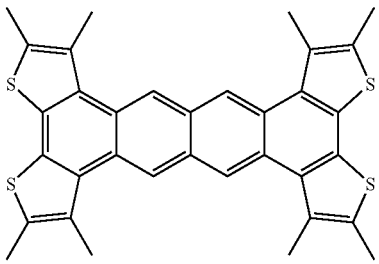

Compound 8

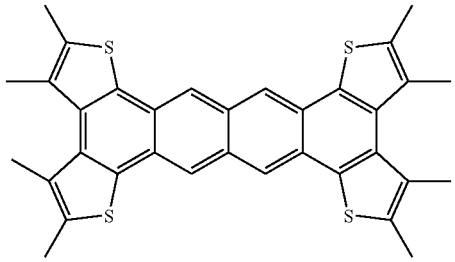

Compound 9

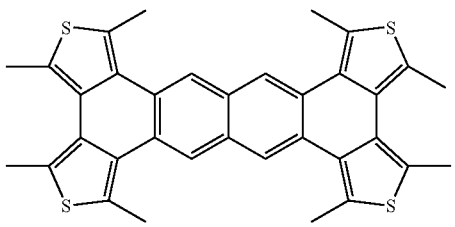

Compound 10

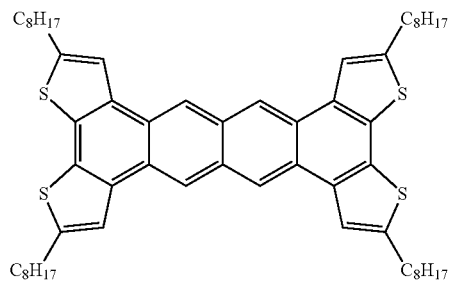

Compound 11

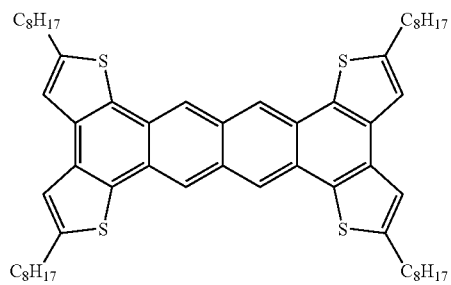

-continued
Compound 12
Compound 13
Compound 14
Compound 15
Compound 16
Compound 17
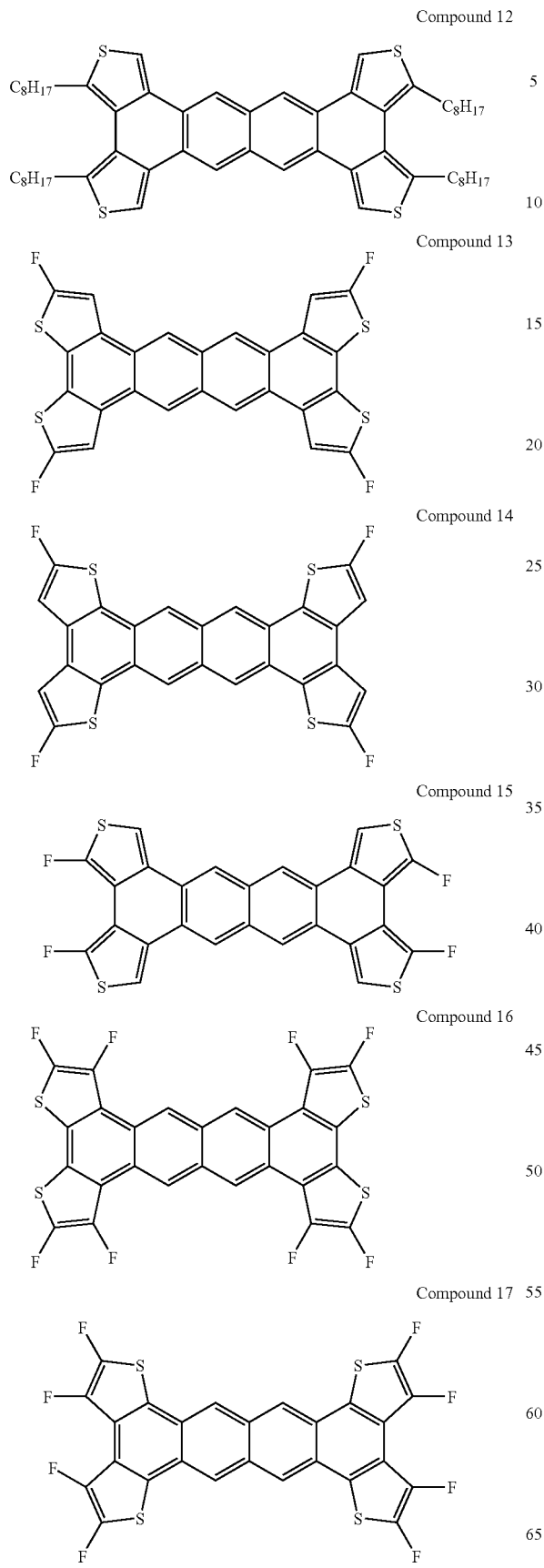
-continued
Compound 18
Compound 19
Compound 20
Compound 21
Compound 22
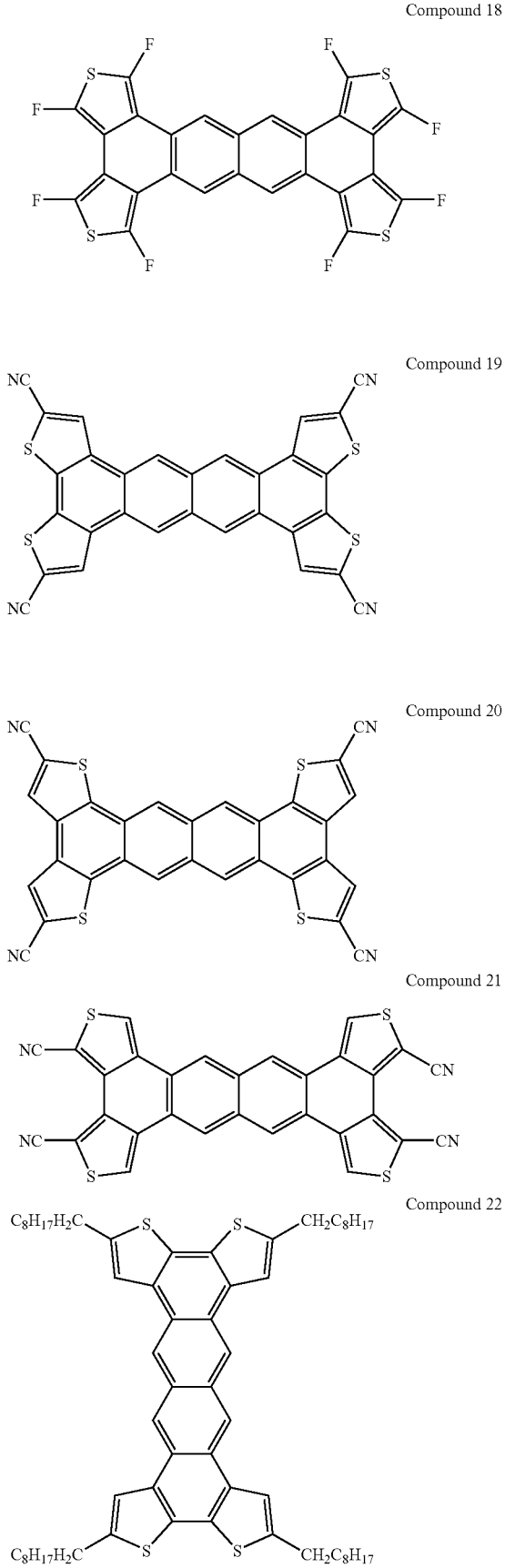

Compound 23
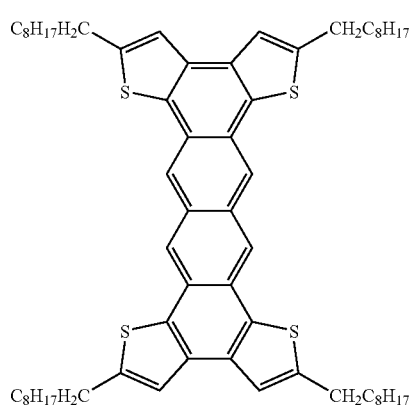
Compound 26
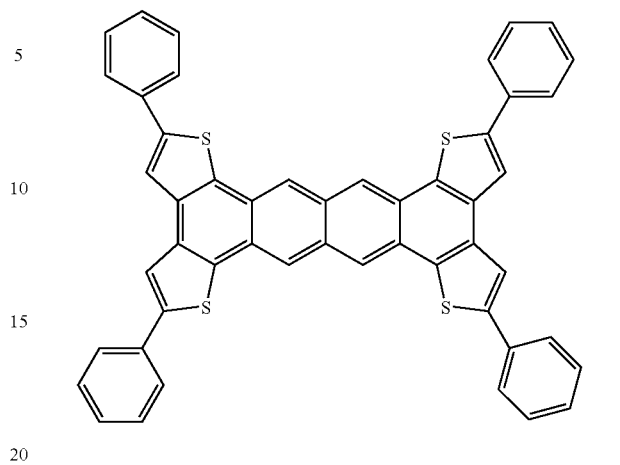
Compound 24
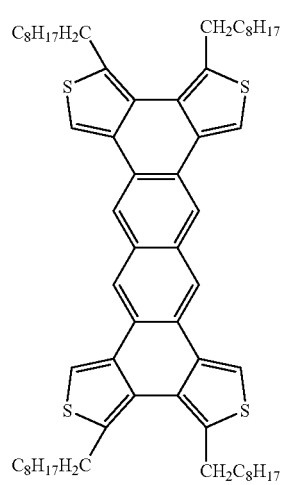
Compound 27
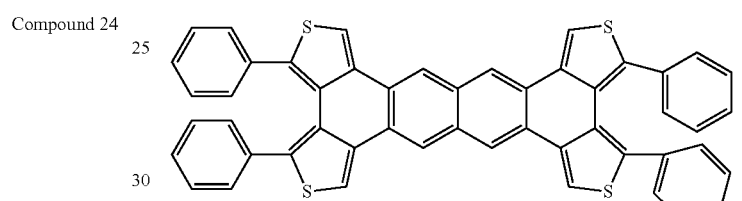
Compound 28
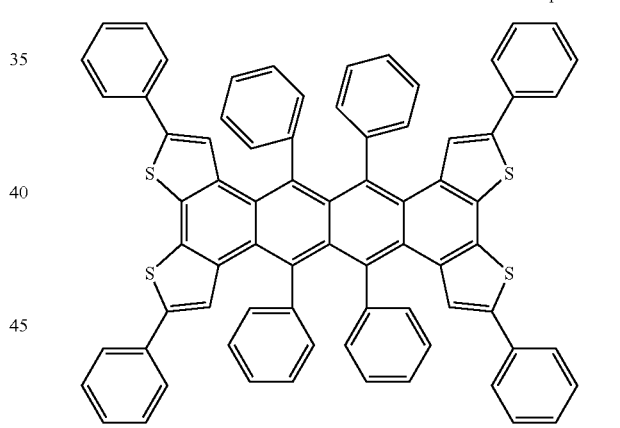
Compound 25
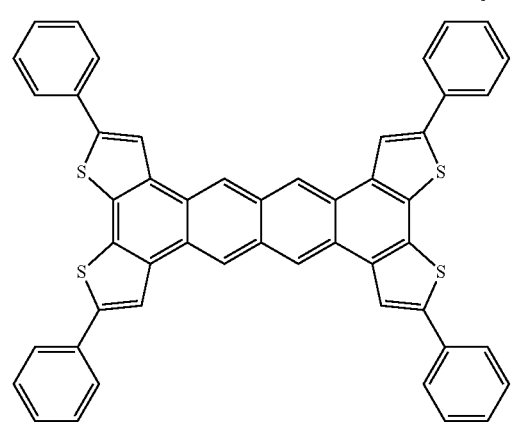
Compound 29
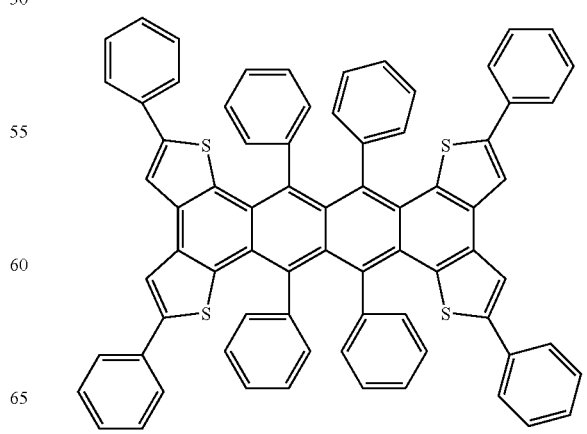

Compound 30

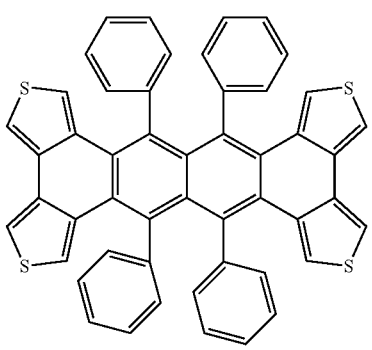

4. The electronic device of claim 1, further comprising a metal conductive material.

5. The electronic device of claim 1, further comprising an organic conductive polymer.

6. The electronic device of claim 5, further comprising carbon nanotubes.

7. A compound represented by Formula 1:

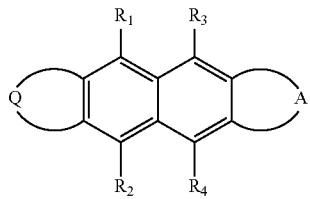

Formula 1 wherein each A and Q are independently selected from the group consisting of

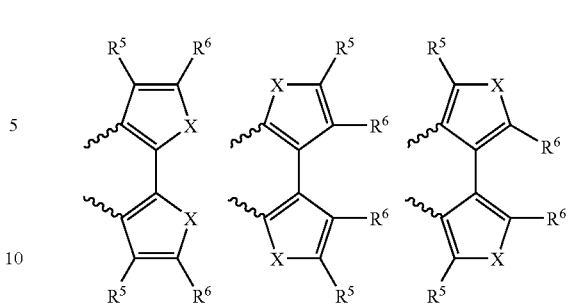

wherein each X is independently selected from the group consisting of S, O, SO, $SO_2$, Se, Te, NR, BR, PR, PO, $PO_2$, and $SiR_2$;

$R^1$-$R^6$ are selected independently from the group consisting of hydrogen; substituted or unsubstituted alkyl; substituted or unsubstituted aryl; substituted or unsubstituted heteroaryl; halogen; hydroxy; substituted or unsubstituted aryloxy; substituted or unsubstituted alkoxy; substituted or unsubstituted alkenyl; substituted or unsubstituted alkynyl; substituted or unsubstituted amino; substituted or unsubstituted alkylthio; substituted or unsubstituted phosphino; substituted or unsubstituted silyl; —COR; —COOR; —$PO_3R_2$; —$OPO_3R_2$; —NC; —$C_nF_{2n+1}$; and —$C_nF_{2n+1}C_mH_{2m+1}$;

R is selected from the group consisting of hydrogen; substituted or unsubstituted alkyl; substituted or unsubstituted aryl; substituted or unsubstituted heteroaryl; substituted or unsubstituted alkenyl; substituted or unsubstituted alkynyl; and substituted or unsubstituted amino;

the substituents on substituted R and $R^1$ through $R^6$ are functional groups selected independently from the group consisting of cyanide; nitro; ester groups; ether groups; halogen; hydroxy; substituted or unsubstituted alkyl groups; substituted or unsubstituted aryl groups; and substituted or unsubstituted alkoxy groups.

* * * * *